United States Patent [19]

Walker et al.

[11] Patent Number: 4,711,888

[45] Date of Patent: Dec. 8, 1987

[54] HYDROXY AND ALKOXY PYRIMIDINES

[75] Inventors: Frederick J. Walker, Groton; John L. LaMattina, Ledyard, both of Conn.

[73] Assignee: Pfizer Inc., New York, N.Y.

[21] Appl. No.: 758,199

[22] Filed: Jul. 24, 1985

[51] Int. Cl.[4] .................. A61K 31/505; C07D 239/47; C07D 401/04

[52] U.S. Cl. .................................... 514/269; 514/275; 544/298; 544/330; 544/331; 544/332

[58] Field of Search ............... 544/330, 331, 332, 298; 514/269, 275

[56] References Cited

U.S. PATENT DOCUMENTS 4,554,276 11/1985 LaMattina ........................... 514/272

OTHER PUBLICATIONS

LaMattina et al., Tetrahedron Letters, vol. 25, pp. 2957-2960 (1984).

LaMattina, Chemical Abstracts, vol. 103, entry 14200u (1985).

LaMattina, Chemical Abstracts, vol. 101, entry 211082v (1984).

Wang et al, Chemical Abstracts, vol. 101, entry 55042z (1984).

Hirata et al, Chemical Abstracts, vol. 67, entry 90759q (1967).

*Primary Examiner*—John M. Ford
*Attorney, Agent, or Firm*—Peter C. Richardson; Lawrence C. Akers; Gezina Holtrust

[57] ABSTRACT

2-Amino-4-substituted-5-(hydroxy or alkoxy)pyrimidines, which may be 6-substituted, and derivatives thereof are inhibitors of leukotriene synthesis and are therefore useful for the treatment of pulmonary, inflammatory, allergic and cardiovascular diseases. The compounds are also cytoprotective and therefore useful in the treatment of peptic ulcers.

17 Claims, No Drawings

HYDROXY AND ALKOXY PYRIMIDINES

BACKGROUND OF THE INVENTION

This invention relates to hydroxy and alkoxy substituted pyrimidines, more particularly, 2-amino and 2-substituted amino-4-substituted-5-(hydroxy or alkoxy)-pyrimidines which are optionally 6-substituted, pharmaceutical compositions containing such compounds as active ingredients and a method of treatment with such compounds.

Bray et al, Biochem. J., 1951, 48, 400, describe 2-amino-4,6-dimethyl-5-hydroxypyrimidine and its preparation without disclosing any pharmaceutical or other utility.

U.K. patent application No. 2045756 discloses 2-isopropylamino-5-hydroxypyrimidine for the treatment of muscular dystrophy. This prior-published application does not disclose any substitution of the mentioned compound at the 4- and 6- positions of the pyrimidine group.

Chemical Abstracts, 94: 121446z (1981) describes 2-dimethylamino-4,6-diphenyl-5-hydroxypyrimidine without disclosing any pharmaceutical or other properties for this compound.

Prior patent application Ser. No. 538,233 filed Oct. 3, 1983 assigned to the same assignee as the present application discloses 2-amino-4-methyl-5-hydroxypyrimidines having similar pharmaceutical utilities as the compounds of the invention.

Current treatment of asthma focuses on the relief of acute bronchospasm through the use of bronchodilators. It is thought that acute bronchospasm is only an overt manifestation of chronic inflammation. Leukotrienes may play a role both in the bronchospasm and the chronic inflammation. They are known to be potent vasodilators and chemotactic agents. They are also produced in allergic reactions and bring about slow contraction of lung tissue in vitro. An inhibitor of leukotriene synthesis should therefore be of use in the treatment of asthma and other pulmonary diseases.

Chronic gastric and duodenal ulcers, together known as peptic ulcers, are the subject of a variety of treatments, including special diets, drug therapy and surgery, depending upon the severity of the condition. Particularly valuable therapeutic agents useful for the treatment of gastric hyperacidity and peptic ulcers are the histamine-$H_2$ receptor antagonists, which block the action of the physiologically-active compound histamine at the $H_2$-receptor sites in the animal body and thereby inhibit the secretion of gastric acid.

SUMMARY OF THE INVENTION

In accordance with the invention, there are provided substituted pyrimidines having the formula:

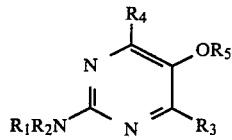

wherein $R_1$ is hydrogen or $(C_1-C_{15})$ alkyl; $R_2$ is hydrogen, $(C_1-C_{15})$alkyl, cyclopentyl, cyclohexyl, $(C_3-C_{15})$alkenyl, phenyl, or $(C_7-C_{20})$phenylalkyl which may be substituted in the phenyl by one or two of fluoro, chloro, $(C_1-C_3)$alkyl, $(C_1-C_3)$alkoxy, or $CF_3$; or $R_1$ and $R_2$ together with the nitrogen atom to which they are attached form a pyrrolidinyl or piperidyl which may be substituted by one $(C_1-C_6)$alkyl, phenyl or $(C_7-C_{20})$-phenylalkyl; $R_3$ is $(C_1-C_6)$alkyl, phenyl, $(C_7-C_{20})$phenylalkyl which may be substituted in the phenyl by one or two fluoro, chloro, $(C_1-C_3)$alkyl, $(C_1-C_3)$alkoxy, or $CF_3$, or furyl or thienyl which may be substituted by one $(C_1-C_3)$alkyl; $R_4$ is hydrogen, $(C_1-C_6)$alkyl, phenyl or $(C_7-C_{20})$phenylalkyl which may be substituted in the phenyl by one or two of fluoro, chloro, $(C_1-C_3)$alkyl, $(C_1-C_3)$alkoxy or $CF_3$; and $R_5$ is hydrogen, $(C_1-C_6)$alkyl, phenyl or $(C_7-C_{20})$phenylalkyl which may be substituted in the phenyl by one or two of fluoro, chloro, $(C_1-C_3)$alkyl, $(C_1-C_3)$alkoxy or $CF_3$; with the provision that when $R_5$ is hydrogen and (1) $R_3$ and $R_4$ are each methyl, then $R_1$ and $R_2$ are not each hydrogen, or (2) $R_3$ and $R_4$ are each phenyl, then $R_1$ and $R_2$ are not each methyl, or (3) $R_3$ is $(C_1-C_6)$alkyl, then $R_4$ is not hydrogen; or an acid addition salt thereof or, when $R_5$ is hydrogen, a base addition salt thereof.

Specific compounds of the invention are those of formula I wherein $R_1$ and $R_5$ are as defined above, $R_2$ is hydrogen, $(C_1-C_{15})$alkyl, phenyl, thienyl, furyl, or $(C_7-C_{20})$phenylalkyl which may be substituted in the phenyl by one or two of chloro or $(C_1-C_3)$alkyl; $R_3$ is $(C_1-C_6)$alkyl, phenyl which may be substituted by one or two fluoro, chloro, methyl, ethyl, methoxy, ethoxy, or $CF_3$; and $R_4$ is hydrogen, $(C_1-C_6)$ alkyl, phenyl or phenyl substituted by one or two methyl or ethyl, and the pharmaceutically acceptable acid addition salts thereof.

In general, $R_2$ is preferably $(C_8-C_9)$ alkyl, $(C_9-C_{12})$-phenylalkyl, $(C_9-C_{12})$p-chlorophenylalkyl or $(C_{10}-C_{13})$p-methylphenylalkyl; $R_3$ and $R_4$ are preferably each methyl; and $R_5$ is preferably $(C_1-C_6)$alkyl.

Specific compounds of the invention are as follows: 2-(p-chlorophenylpropylamino)-4,6-dimethyl-5-hydroxypyrimidine, 2-(p-methylphenylpropylamino)-4,6-dimethyl-5-hydroxypyrimidine, 2-(n-nonylamino)-4,6-dimethyl-5-hydroxypyrimidine, 2-phenylhexylamino-4,6-dimethyl-5-hydroxypyrimidine, 2-dimethylamino-4-p-fluorophenyl-5-hydroxyprimidine, 2-phenylhexylamino-4-methyl-5-methoxypyrimidine, 2-dimethylamino-4-(3,-4-dichlorophenyl)-5-methoxypyrimidine, 2-dimethylamino-4-(3,4-dichlorophenyl)-5-ethoxypyrimidine, 2-(p-chlorophenylpropyl)-4,6-dimethyl-5-methoxypyrimidine, 2-phenylhexylamino-4,6-dimethyl-5-methoxypyrimidine, and 2-phenylpentylamino-4,6-dimethyl-5-methoxypyrimidine.

The invention includes pharmaceutical compositions comprising a pharmaceutically acceptable carrier or diluent and a compound of the formula I',

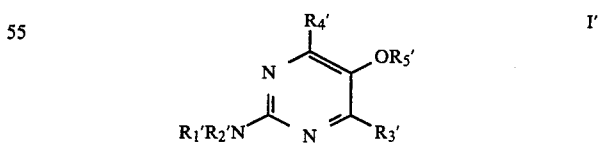

or a pharmaceutically acceptable acid addition salt thereof or, when $R_5$ is hydrogen, a pharmaceutically acceptable base addition salt thereof, in an amount effective for the treatment of pulmonary, asthmatic, allergic, inflammatory or gastrointestinal diseases, in admixture with a pharmaceutically acceptable carrier, wherein $R_1'$ is hydrogen or $(C_1-C_{15})$alkyl; $R_2'$ is hydrogen, $(C_1-C_{15})$alkyl, cyclopentyl, cyclohexyl, ($C_3$–$C_{15}$)alkenyl, phenyl, or ($C_7$–$C_{20}$)phenylalkyl which may be substituted in the phenyl by one or two of fluoro, chloro, ($C_1$–$C_3$)alkyl, ($C_1$–$C_3$) alkoxy, or $CF_3$; or $R_1'$ and $R_2'$ together with the nitrogen atom to which they are attached form a pyrrolidinyl or piperidyl which may be substituted by one ($C_1$–$C_6$)alkyl, phenyl or ($C_7$–$C_{20}$) phenylalkyl; $R_3'$ is ($C_1$–$C_6$)alkyl, phenyl, or ($C_7$–$C_{20}$) phenylalkyl which may be substituted in the phenyl by one or two fluoro, chloro, ($C_1$–$C_3$)alkyl, ($C_1$–$C_3$)alkoxy, or $CF_3$, or furyl or thienyl which may be substituted by one ($C_1$–$C_3$) alkyl; $R_4'$ is hydrogen, ($C_1$–$C_6$)alkyl, phenyl or ($C_7$–$C_{20}$)phenylalkyl which may be substituted in the phenyl by one or two of fluoro, chloro, ($C_1$–$C_3$)alkyl, ($C_1$–$C_3$)alkoxy or $CF_3$; and $R_5'$ is hydrogen, ($C_1$–$C_6$) alkyl, phenyl or ($C_7$–$C_{20}$) phenyl alkyl which may be substituted in the phenyl by one to three of fluoro, chloro, ($C_1$–$C_3$)alkyl, ($C_1$–$C_3$)alkoxy or $CF_3$; with the proviso that when $R_4'$ and $R_5'$ are each hydrogen then $R_3'$ is not ($C_1$–$C_6$)alkyl.

Specific compositions of the invention contain the specific compounds mentioned above and preferred compositions contain the compounds having the above generally preferred meanings of $R_2$, $R_3$, $R_4$ and $R_5$ for corresponding radicals $R_2'$, $R_3'$, $R_4'$ and $R_5'$, respectively.

The invention further includes a method of treating a host affected by pulmonary, asthmatic, allergic or inflammatory diseases with a compound of the formula I' as defined above or a pharmaceutically acceptable acid addition salt thereof or, when $R_5'$ is hydrogen, a pharmaceutically acceptable base addition salt thereof, The term "alkyl" in the definitions of groups $R_1$, $R_2$, $R_3$, $R_4$, $R_5$, $R_1'$, $R_2'$, $R_3'$, $R_4'$, and $R_5'$ denotes saturated monovalent straight or branched aliphatic hydrocarbon radicals such as methyl, ethyl, propyl, butyl, t-butyl, hexyl, octyl, 2-ethylhexyl etc.

The term "phenylalkyl" in the definitions of groups $R_2$, $R_3$, $R_4$, $R_5$, $R_2'$, $R_3'$, $R_4'$ and $R_5'$ denotes a phenyl group attached to saturated divalent straight or branched aliphatic hydrocarbon radicals. Examples of such phenylalkyls are methylphenyl, ethylphenyl, propylphenyl, butylphenyl, pentylphenyl, hexylphenyl, octylphenyl, 1,1-dimethyl-7-phenylheptyl etc.

DETAILED DESCRIPTION OF THE INVENTION

The reaction scheme hereafter sets out several of the processes by which the compounds of formula I of the invention may be prepared. The compounds of formula I' differ from the compounds of formula I in the proviso clause excluding the compounds of above-mentioned U.S. Pat. No. 4,554,276. The proviso clause of formula I excludes the above Bray et al compound and the above Chemical Abstracts compound as well as the compounds of U.S. Pat. No. 4,554,276. The description below for the preparation of compounds of formula I equally applies to compounds of formula I'.

The compounds of formula I may be prepared by condensing a diketoacyloxy compound of formula II wherein $R_3$ and $R_4$ are as defined above and acyl is any acyl group such as acetyl or benzoyl, with a 1,1-($R_1,R_2$)guanidine salt of formula II wherein $R_1$ and $R_2$ are each hydrogen or ($C_1$–$C_6$) alkyl. The condensation is carried out in the presence of an alkaline reagent such as sodium acetate, sodium hydroxide or sodium ethoxide, and an aprotic polar solvent such as dimethylformamide, dimethylsulfoxide or aqueous alcohol, at a temperature of 80° to 140° C., usually 100° C., for a time period of about 2 to 24 hours, usually 3 to 5 hours.

The compounds of formula IV formed are treated with a hydride reducing agent to form the corresponding 5-hydroxypyrimidines of formula I. Specific hydride reducing agents are for instance diisobutylaluminum hydride (Dibal®) and sodium bis(2-methoxyethoxy)aluminum hydride. The reaction is generally carried out at −78° to −10° C., usually about −23° C., in a dry inert solvent such as tetrahydrofuran, ether, toluene or benzene.

Alternatively, compounds (IV) may be hydrolyzed to compounds (I) by usual techniques such as reaction with aqueous or alcoholic alkali.

The compounds of formula I wherein $R_1$ is hydrogen and $R_2$ is ($C_7$–$C_{20}$) phenylalkyl may be prepared by reacting a compound (II) as defined above with guanidine to form a compound of formula V wherein $R_3$ and $R_4$ are as previously defined. The reaction conditions are as outlined above with respect to condensation of compounds (II) with compounds (III).

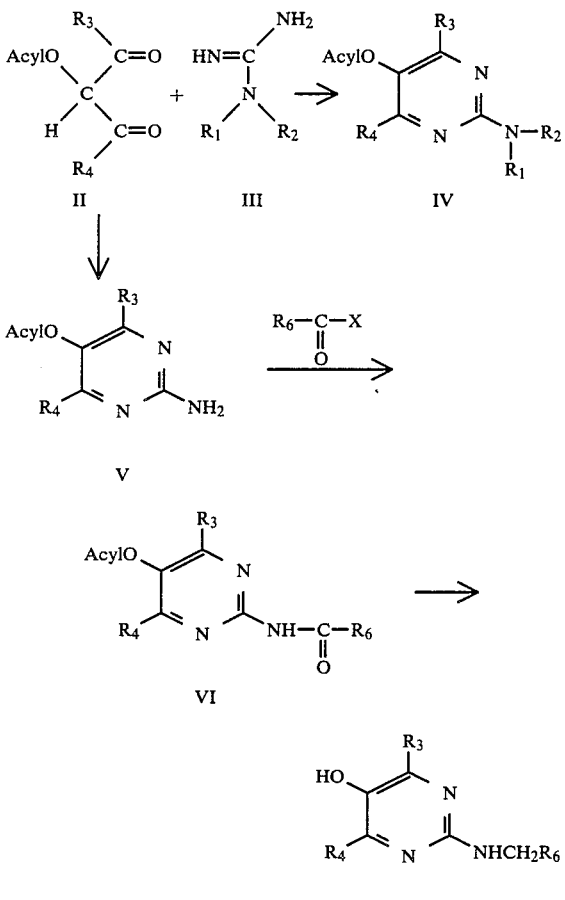

The formed compound (V) is then reacted with a phenylalkanoic acid halide of the formula $$R_6-\underset{\underset{O}{\|}}{C}-X$$

wherein X is halogen, preferably chlorine, and $R_6$ is ($C_6$–$C_{19}$)phenylalkyl which may be substituted in the phenyl group by one to three of fluoro, chloro, ($C_1$–$C_6$)alkyl, ($C_1$–$C_6$)alkoxy, or trifluoromethyl. This reaction to form compound (VI) is carried out in general at $-20°$ C. to room temperature, usually about $0°$ C., for at least 15 minutes, for instance about half an hour, depending on the reaction temperature. The reaction may be speeded up by heating the reaction mixture after addition of all of the halide to about $20°$ to $30°$ C., e.g. $25°$ C., for at least about 15 minutes, usually 0.5 hour.

The corresponding compound of formula VII is formed by reacting compound (VI) with a hydride reducing agent such as diisobutylaluminum hydride or sodium bis(2-methoxyethoxy)aluminum hydride. The reaction is generally carried out at $-78°$ to $-10°$ C., e.g. at about $-23°$ C., in a dry inert solvent such as tetrahydrofuran, ether, toluene or benzene.

Alternatively, compound (V) may be reacted with an agent of the formula $R_1X$ or $R_2X$ wherein $R_1$ and $R_2$ are as defined above and X is mesylate or halogen such as chlorine, bromine or iodine. The reaction conveniently proceeds in the presence of a base such as sodium hydroxide, t-butoxide, sodium hydride or tertiary amines such as triethylamine.

The compounds of formula I wherein $-NR_1R_2$ is an optionally substituted pyrrolidinyl or piperidyl ring may be formed by reaction of the corresponding compound (I) wherein $R_1$ and $R_2$ are hydrogen with a dihalide such as 1,4-dibromobutane or 1,5-dibromopentane or properly substituted derivatives thereof. Alternatively, compound (I) wherein the $NR_1R_2$ group is replaced with methylsulphonyl is reacted with an amine of the formula $R_1R_2NH$ wherein $R_1$ and $R_2$ together with the nitrogen to which they are attached are pyrrolidinyl or piperidinyl which may be substituted by one or two of ($C_1$–$C_6$)alkyl, phenyl or ($C_7$–$C_{20}$) phenylalkyl which may be substituted in the phenyl by ($C_1$–$C_6$) alkyl. This method is described in Brown et al., The Pyrimidines, Supplement I, 226 and 227, Wiley-Interscience (1970).

The compounds of formula I wherein $R_5$ is other than hydrogen are formed by reacting the corresponding compound wherein $R_5$ is hydrogen (VIII) with a compound of the formula $R_5X$ wherein X is a group which easily reacts with the hydroxyl group in compound VIII, for instance halogen such as chlorine, tosyl or mesyl. When $R_5$ is methyl, methylating agents such as dimethylsulfate may be used as well.

The reaction is generally carried out under anhydrous conditions in an aprotic, polar solvent such as tetrahydrofuran, dimethylformamide, or dimethylsulfoxide. Suitable reaction temperatures range from about $0°$ to about $100°$ C., usually $25°$ to $30°$ C. The reaction is facilitated by forming the phenolate salt of compounds (VIII) by conducting the reaction in the presence of a base including an organic base such as triethylamine, and an inorganic base such as sodium hydroxide or potassium hydroxide. In that case, the reaction is conducted in an inert atmosphere such as nitrogen to avoid oxidation of the phenolate anion.

The diketo-acyloxy compounds of formula II may be prepared by acylation of a corresponding diketo-halo compound as described by Barillier, D., et al., Bull. Soc. Chim., 1976, 444–448. Thus, 1,3-disubstituted-2-halopropanedione-1,3 is reacted with a sodium acylate in a solvent such as dimethylsulfoxide. The halogen in the diketo compound is chloro or bromo. The acylate may be any suitable acylate such as an acetate or benzoate.

The diketo-halo compounds may be prepared by halogenation of the corresponding diketones, whereas these diketones may be prepared by known methods such as described by Levine, R., et al., J. Am. Chem. Soc., 67, 1510–1512 (1945). Thus, beta-diketones are formed by acylation of ketones with esters by means of sodium amide.

The guanidine salts of formula III used for the preparation of compounds of formula I are commercially available when $R_1$ and $R_2$ are either hydrogen or methyl.

The acid addition salts of the compounds of formula I are prepared in a conventional manner by treating a solution or suspension of the free base (I) with about one chemical equivalent of a pharmaceutically acceptable acid. Conventional concentration and recrystallization techniques are employed in isolating the salts. Illustrative of suitable acids are acetic, lactic, succinic, maleic, tartaric, citric, gluconic, ascorbic, benzoic, cinnamic, fumaric, sulfuric, phosphoric, hydrochloric, hydrobromic, hydroiodic, sulfamic, sulfonic such as methanesulfonic, benzensulfonic, and related acids. Preferably, the acid is phosphoric acid.

The base addition salts of compounds (I) wherein $R_5$ is hydrogen may be prepared in a conventional manner by reacting the phenol (I) with about one chemical equivalent of inorganic base such as an alkali metal hydroxide or an alkaline earth metal hydroxide.

The compounds of formula I' and their pharmaceutically acceptable acid addition and base addition salts are inhibitors of leukotriene synthesis and agents for the treatment of various pulmonary, gastrointestinal, inflammatory, dermatological and cardiovascular conditions. In particular, the compounds have utility, both as the sole active agent and also in combination with other active agents, for the treatment of asthma, bronchitis, pulmonary diseases such as pulmonary hypertension and hypoxia, peptic ulcers, psoriasis, arthritis, inflammatory bowel disease or cardiovascular spasm, such as acute myocardial infarctions.

For treatment of the various conditions described above the compounds of formula I' may be administered to a subject in need of treatment by a variety of conventional routes of administration, including oral, by injection, topical, and in an aerosol carrier composition for administration by breathing.

In general, a therapeutically-effective dose for the active compounds of formula I' will range from 0.01 to 100 mg/kg body weight of the subject to be treated per day, preferably 0.1 to 50 mg/kg per day.

Although the compounds of formula I' can be administered alone, they will generally be administered in admixture with a pharmaceutical carrier selected with regard to the intended route of administration and standard pharmaceutical practice. For example, oral administration may be in the form of tablets containing such excipients as starch or lactose, or in capsules either alone or in admixture with excipients, or in the form of elixirs or suspensions containing flavoring or coloring agents. In the case of animals, they are advantageously contained in an animal feed or drinking water. For parenteral injection, they may be used in the form of a sterile aqueous solution which may contain other solutes, for example enough salt or glucose to make the solution isotonic.

The activity of the compounds of formula I' in the treatment of pulmonary, asthmatic, allergic and inflammatory diseases may be determined by a standard test measuring an agent's ability to inhibit cyclooxygenase and lypoxygenase enzyme activity of rat basophil leukemia (RBL-1) cells. According to this test as described by Jakschick et al., Prostaglandins 16,733–747 (1978), a monolayer of RBL-1 cells is grown for 1 or 2 days in spinner culture in Eagle's minimum essential medium, 15% heat-inactivated fetal calf serum and an antibiotic/antimycotic mixture. The cells are washed after centrifugation and incubated in a buffer. A volume of 0.5 ml of cell suspension is preincubated at 30° C. for ten minutes with a 1 μl dimethylsulfoxide (DMSO) solution of the agent to be tested. The incubation is initiated by simultaneous addition of 5 1 ($^{14}$C)- arachidonic acid in ethanol and 2 μl calcium ionophore (A-21387) in DMSO for final concentrations of 5 and 7.6μM, respectively. Five minutes later, the incubation is terminated by the addition of 0.27 ml acetonitrile/acetic acid (100:3). Thin layer chromatography is performed using acetonitrile/water/acetic acid solvent.

The following Examples illustrate the invention.

EXAMPLE 1

2-(p-Chlorophenylpropylamino)-4,6-dimethyl-5-hydroxypyrimidine ($R_1 = R_5 = H$; $R_2$ = p-chlorophenylpropyl; $R_3 = R_4$ = methyl)

5-Acetoxy-4,6-dimethyl-2-(p-chlorophenylpropylamido)pyrimidine (0.27 g, 0.78 mmol) was treated with 3.5 ml (3.5 mmol) of a one molar solution of Dibal in hexane at −23° C. in dry tetrahydrofuran (5 ml) under nitrogen for 3 hours. The reaction mixture was quenched with 15 ml aqueous ammonium chloride and stirred at room temperature overnight.

The reaction mixture was then filtered and the filtrate extracted with a total of 40 ml of ethyl acetate. The extracts were dried, concentrated and chromatographed with hexane and ethyl acetate (1:1) to yield 0.1 g (37%) of crystalline title compound, m.p. 124°–126° C.

EXAMPLE 2

2-(p-Methylphenylpropylamino)-4,6-dimethyl-5-hydroxypyrimidine ($R_1$ = H, $R_2$ = p-methylphenylpropyl; $R_3 = R_4$ = methyl; $R_5$ = hydrogen)

5-Acetoxy-4,6-dimethyl-2-(p-methylphenylpropylamido)pyrimidine (7.7 g, 24 mmol) was treated with a one molar solution of Dibal in hexane (94 ml, 94 mmol) in a dry solution of tetrahydrofuran (150 ml) at −35° C. under nitrogen. After 3.5 hours, the reaction mixture was quenched with saturated aqueous ammonium chloride (100 ml), brought to room temperature and stirred for one hour. Filtration gave a clear solution which was diluted with 100 ml water and extracted with 250 ml ethyl acetate. The dried extracts were concentrated and chromatographed on silica gel (1:1, hexane and ethylacetate) to yield 2.0 g (31%) of the title compound, m.p. 103°–104° C.

EXAMPLE 3

In a similar manner as in Example 1, the following compounds were prepared:

2-(n-nonylamino)-4,6-dimethyl-5-hydroxypyrimidine;
NMR(CDCl$_3$): 0.8–1.6 (m, 17H), 2.25 (s, 6H), 3.1–3.4 (m, 2H);

4,6-dimethyl-5-hydroxy-2-phenylhexylaminopyridine; m.p. 43°–45° C.

4-isopropyl-5-hydroxy-6-methyl-2-p-chlorophenpropylaminopyrimidine; NMR(CDCl$_3$): 7.10 (m, 4H), 4.20 (b s, 1H), 3.30 (m, 3H), 2.6 (m, 2H), 2.3 (s, 3H), 1.80 (m, 2H), 1.2 (d, 6H); and 4-isopropyl-5-hydroxy-6-methyl-2-nonylaminopyrimidine; NMR(CDCl$_3$) 6.30 (b s, 1H), 4.75 (b s, 1H), 3.55–3.10 (m, 3H), 2.30 (s, 3H), 1.60–0.90 (m, 23H).

EXAMPLE 4

A. A mixture of 3-acetoxy-5-methyl-2,4-hexanedione (5 g, 27 mmol) and guanidine acetate (6.4 g, 54 mmol) in 100 ml dimethylformamide (DMF) was heated at 100° C. for 3 hours. After cooling, the concentrated reaction was filtered through a pad of silica gel using an eluent consisting of equal volume parts of hexane and ethylacetate. The filtrate was concentrated and the residue was treated with excess acetic anhydride in the presence of triethylamine. The reaction mixture was concentrated and the residue was crystallized from boiling hexane to yield 1.7 g (31%) 5-acetoxy-2-amino4-isopropyl-6-methylpyrimidine, m.p. 141°–142° C.

B. 5-Acetoxy-2-amino-4-isopropyl-6-methylpyrimidine (0.5 g, 2.4 mmol) in pyridine was treated with 6-phenylhexanoic acid chloride (3.6 mmol) at 0° C. for 0.5 hours. The reaction mixture was warmed to 25° C. and held at that temperature for 0.5 hours. The reaction mixture was concentrated and the residue chromatographed on silica gel in an eluent of hexane and ethylacetate (3:1) to give 0.66 g (72%) of 5-acetoxy-4-isopropyl-6-methyl-2-phenylhexylamidopyrimidine.

NMR(CDCl$_3$) 8.28 (b s, 1H), 7.20 (s, 5H), 3.20–2.50 (m, 5H), 2.35 (s, 3H), 2.25 (s, 3H), 1.90–1.40 (m, 6H), 1.08 (d, 6H).

C. The compound prepared under B was reacted by the process of Example 3 to form 4-isopropyl-5-hydroxy-6-methyl-2-phenylhexylaminopyrimidine, m.p. 60°–61° C.

EXAMPLE 5

2-Dimethylamino-4-isopropyl-6-methyl-5-hydroxypyrimidine ($R_1 = R_2$ = methyl; $R_3$ = isopropyl, $R_4$ = methyl)

A. 3-Acetoxy-5-methyl-2,4-hexadione (3 g, 16 mmol), 1,1-dimethylguanidine sulfate (4.4 g, 16 mmol) and sodium acetate (2.6 g, 32 mmol) were combined in dimethylformamide and heated in nitrogen atmosphere at 100° C. for 4 hours. The reaction mixture was cooled and concentrated. Chromatography on silica gel (9:1, hexane: ethyl acetate) provided 0.4 g of a brown oil, 5-acetoxy-2-dimethylamino-4-isopropyl-6-methylpyrimidine.

NMR(CDCl$_3$): 3.2 (s, 6H), 3.0–2.5 (s, 3H), 2.1 (s, 3H), 1.1 (d, 6H).

B. The compound prepared under A above (0.3 g, 1.3 mmol) was dissolved in dry tetrahydrofuran, cooled to −35° C. in a nitrogen atmosphere and treated with a one molar solution of Dibal (2.6 ml, 2.6 mmol) in hexane. After one hour, the reaction temperature was raised to 0° C. over one hour and quenched with 10 ml aqueous ammonium chloride. The mixture was filtered, extracted with 25 ml ethyl acetate, dried over magnesium sulfate and concentrated to yield 0.24 g of the title compound, m.p. 82°–83° C.

EXAMPLE 6

Following the method in Example 5B, 2-dimethylamino-4-methyl-6-phenyl-5-hydroxypyrimidine, m.p. 125.5° to 127.5° C., was formed from 2-dimethylamino-4-methyl-6-phenyl-5-acetoxypyrimidine, NMR(CDCl$_3$): 8.3–7.3 (m, 5H), 3.3 (s, 6H), 2.3 (s, 3H), 2.1 (s, 3H) prepared by the method of Example 5A.

EXAMPLE 7

Similar to the method in Example 4B, the following intermediate compounds were formed:

5-acetoxy-2-p-chlorophenylpropylamino-4-isopropyl-6-methylpyrimidine; NMR(CDCl$_3$) 7.20 (s, 4H), 3.3–2.7 (m, 5H), 2.35 (s, 3H), 2.30 (s, 3H), 1.21 (d, 6H); and 5-acetoxy-2-n-nonyl-4-isopropyl-6-methylpyrimidine; NMR(CDCl$_3$) 3.5–2.8 (m, 3H), 2.35 (s, 3H), 2.30 (s, 3H), 1.5–0.8 (m, 21H).

EXAMPLE 8

2-(p-Chlorophenylpropylamino)-4-phenyl-5-hydroxypyrimidine

2-Amino-5-benzoyloxazole (3.0 g, 16 mmol) was combined with p-chlorophenylpropylamine (2.7 g, 16 mmol) in 15 ml of water and t-butanol (2:1) and heated under reflux in nitrogen for 16 hours. The solvents were removed in a vacuum, and the residue was treated with hot acetonitrile and filtered. After concentration in vacuum, the filtrate was chromatographed on silica gel using hexane and ethyl acetate (1:1) as eluent to give 0.24 mg (4.4%) of the title compound as an oil. NMR (CDCl$_3$): 1.8–2.0 (m, 2H), 2.4–2.7 (m, 2H), 3.1–3.4 (m, 2H), 5.0 (b s, 1H), 7.0–7.5 (m, 7H), 7.8 (s, 1H), 7.9–8.0 (m, 2H).

EXAMPLE 9

Similar to the method in Example 8, the following compounds were prepared:

TABLE

| R$_1$ | R$_2$ | R$_4$ | Melting Point (°C.) |
|---|---|---|---|
| CH$_3$ | CH$_3$ | phenyl | 143–144 |
| CH$_3$ | CH$_3$ | 4-methoxyphenyl | 153–154 |
| CH$_3$ | CH$_3$ | 2,4-dichlorophenyl | 143–144 |
| H | H | phenyl | 186–187 |
| H | (CH$_2$)$_6$phenyl | 2-fluorophenyl | * |
| CH$_3$ | CH$_3$ | 2-fluorophenyl | 108–109 |
| CH$_3$ | CH$_3$ | 4-methylphenyl | 183–184 |
| H | (CH$_2$)$_8$CH$_3$ | 4-chlorophenyl | 154–155 |
| CH$_3$ | CH$_3$ | 4-chlorophenyl | 163–164 |
| CH$_3$ | CH$_3$ | 3-CF$_3$—phenyl | 146–147 |
| H | (CH$_2$)$_6$CH$_3$ | 4-methylphenyl | 77–78 |
| CH$_3$ | CH$_3$ | 3-bromophenyl | 134–135 |
| H | (CH$_2$)$_8$CH$_3$ | 3-CF$_3$—phenyl | 48–50 |
| CH$_3$ | CH$_3$ | 4-ethylphenyl | 135–136 |
| H | (CH$_2$)$_8$CH$_3$ | 3,4-dichlorophenyl | 69–70 |
| H | (CH$_2$)$_6$CH$_3$ | 4-chlorophenyl | 84–85 |
| CH$_3$ | CH$_3$ | 2-thienyl | 171–172 |
| CH$_3$ | CH$_3$ | 2-furyl | 169–171 |
| CH$_3$ | CH$_3$ | 3-thienyl | 167–169 |

*NMR (CDCl$_3$): 7.75 (s, 1H), 7.0 (m, 9H), 5.8 (b s, 1H), 4.8 (b s, 1H), 3.2 (m, 2H), 2.5 (m, 2H), 1.5 (m, 8H).

EXAMPLE 10

4-(3,4-Dichlorophenyl)-2-dimethylamino-5-hydroxypyrimidine

2-Amino-5-(3′,4′-dichlorobenzoyl)oxazole (2 g, 7.8 mmol) was combined with aqueous dimethylamine (100 ml) in t-butyl alcohol and stirred at room temperature for 4 hours. The solvents were removed in vacuum and the residue was chromatographed on silica gel with hexane and ethylacetate (3:1) as the eluent to yield 1.5 g of the title compound as a crystalline solid, m.p. 188°–189° C.

EXAMPLE 11

In a similar manner as in Example 8, the following compounds were prepared:

2-(n-nonylamino)-4-phenyl-5-hydroxypyrimidine; NMR(CDCl$_3$): 0.9–1.7 (m, 17H), 3.1–3.6 (m, 2H), 7.35–7.55 (m, 3H), 7.8 (s, 1H), 8.0–8.25 (m, 2H);

2-dimethylamino-4-(4-fluorophenyl)-5-hydroxypyrimidine; m.p. 159°–160° C.;

2-phenylhexylamino-4-phenyl-5-hydroxypyrimidine; NMR(CDCl$_3$): 1.4 (m, 8H), 2.5 (m, 2H), 3.38 (b s, 1H), 4.8 (b s, 1H), 6.95–7.4 (m, 8H), 7.8 (s, 1H), 7.9–8.1 (m, 2H); and 2-(n-hexylamino)-4-phenyl-5-hydroxypyrimidine; NMR(CDCl$_3$); 8.2–8 (m, 2H), 7.8 (s, 1H), 7.4–7.2 (m, 3H), 5.0 (b s, 1H), 3.3 (m, 2H), 1.5–0.9 (m, 11H).

EXAMPLE 12

4,6-Dimethyl-5-methoxy-2-phenylpentylaminopyrimidine (R$_1$=H; R$_2$=2-phenpentyl; R$_3$=R$_4$=R$_5$=CH$_3$)

4,6-Dimethyl-5-hydroxy-2-phenpentylaminopyrimidine (0.5 g, 1.8 mmol) prepared by the method of example 1 was dissovled in dry THF (20 ml) under nitrogen and treated with sodium hydride (0.07 g, 1.8 mmol, 60% oil dispersion). The reaction mixture was stirred at 0° C. for 2 hours. Dimethylsulfate (0.11 ml, 1.8 mmol) added with a syringe and the reaction was stirred for an additional hour. After quenching with saturated NH$_4$Cl (aqueous, 20 ml), the reaction mixture was extracted with ethylacetate (75 ml). The extracts were washed with 50 ml water and 50 ml brine, dried over MgSO$_4$ and concentrated. Chromatography on silica gel with ethylacetate/hexane (1:1) eluent yielded 0.15 g of the title compound as a yellow oil, m.p.: 31° to 33° C.

NMR(CDCl$_3$) 7.2 (s, 5H), 3.6 (s, 3H), 3.4 (m, 2H), 2.6 (m, 2H), 2.3 (s, 6H), 1.6–1.4 (m, 6H).

EXAMPLE 13

By the method of Example 12, 4,6-dimethyl-5-methoxy-2-phenylhexylaminopyrimidine was prepared.

NMR(CDCl$_3$) 7.14 (bs, 5H), 4.9 (b s, 1H), 3.63 (s, 3H), 3.4 (m, 2H), 2.6 (m, 2H), 2.3 (s, 6H), 1.3–1.4 (m, 8H).

EXAMPLE 14

5-Methoxy-4-methyl-2-phenylhexylaminopyrimidine (R$_1$=H; R$_2$=2-phenylhexyl: R$_3$=H; R$_4$=R$_5$=CH$_3$)

Sodium hydride (60% oil disperson, 58 mg, 1.45 mmol) was washed twice with pentane in a dry, nitrogen-filled flask. The residue was slurried in 4 ml dry THF and 320 mg (1.1 mmol) of 5-methoxy-4-methyl-2-phenylhexylaminopyrimidine was added portionwise at 0° C. After stirring for a half hour, dimethylsulfate was added. The reaction mixture was cooled to room temperature over one hour, then diluted with 10 ml saturated ammonium chloride and extracted four times each with 25 ml ethyl acetate. The extracts were combined, dried over magnesium sulfate, and concentrated to 374 mg of an oil. Chromatography on silica gel with ethyl acetate/hexane (1:1) provided 130 mg of an oil which crystallized on standing. The crystallized title compound had a melting point of 39° to 40° C.

EXAMPLE 15

Similar to the method of Example 14, 4-(3,4-dichlorophenyl)-2-dimethylamino-5-methoxypyrimidine was prepared, m.p. 72°–73° C.; 4-(3,4-dichlorphenyl)-2-dimethylamino-5-ethoxypyrimidine, m.p. 69°–70° C.; and 2-(p-chlorophenpropylamino)-4,6-dimethyl-5-methoxypyrimidine, m.p. 84°–85° C.;

EXAMPLE 16

2-Dimethylamino-4-methyl-5-benzyloxypyrimidine ($R_1=R_2=R_4=CH_3$; $R_3=H$; $R_5=$benzyl)

Potassium hydroxide (85%, 2.64 g, 40 mmol) was powdered and added to 20 ml of DMSO at room temperature. 2-Dimethylamino-4-methyl-5-hydroxypyrimidine (1.53 g, 10 mmol) was added and the reaction mixture stirred for 5 minutes at room temperature. Benzylbromide (1.2 ml, 10 mmol) was added and the reaction mixture after stirring for a half hour at room temperature was poured into 50 ml of water. The reaction mixture was extracted four times with 50 ml hexane portions. The combined hexane extracts were dried over $Na_2SO_4$, filtered, and evaporated. Recrystallization of the formed solid from hexane yielded 1.8 g (75% yield) of the title compound as pale yellow crystals, m.p. 73° to 74° C.

EXAMPLE 17

Similar to the method of Example 16, 2-dimethyl amino-4-methyl-5-methoxypyrimidine was prepared having a melting point of 189° to 190° C. (hydrochloride salt).

EXAMPLE 18

Ethyl 2-(2-dimethylamino-5-methoxypyrimidine-4-yl)-acetate ($R_1=R_2=R_5=CH_3$; $R_3=H$; $R_4=CH_2CO_2C_2H_5$)

A three-necked 150 ml flask fitted with a septum, a low temperature thermometer and an addition funnel was charged under nitrogen with 11.6 ml (18.6 mmol) of 1.6 M n-butyllithium. After cooling the flask to 5° C., a solution of 2.6 ml (18.6 mmol) of diisopropylamine in 20 ml dry THF was added dropwise over 5 minutes. After addition was completed, the mixture was stirred at 5° C. for 15 minutes and then cooled to −70° C. To the reaction mixture was added a solution of 1.56 g (9.3 mmol) of 2-dimethylamino-4-methyl-5-methoxypyrimidine in 20 ml dry THF over ten minutes. The reaction mixture was then stirred at −70° C. for 1.5 hour, and a solution added of 2.0 g (18.6 mmol) of ethyl chloroformate in 20 ml dry THF over five minutes. The reaction mixture was stirred at −70° C. for a half hour and then allowed to warm to −15° C. over 15 minutes. The reaction mixture was poured into 100 ml of water, the aqueous mixture brought to pH 8.5 with 1N HCl and extracted with three 25 ml portions of chloroform. The combined extracts were dried over $Na_2SO_4$, filtered and evaporated leaving an oil. Chromatography over 100 g of silica gel with hexane/ethyl acetate (9:1) yielded 47% (1.05 g) of the title compound as a colorless liquid.

$NMR(CDCl_3)$ 8.0 (s, 1H), 4.19 (q, J=7 Hz, 2H), 3.75 (s, 3H), 3.65 (s, 2H), 3.05 (s, 6H), 1.1 (t, J=7 Hz, 3H).

EXAMPLE 19

2-Phenylhexylamino-4-methyl-5-hydroxypyrimidine sodium salt

Sodium hydride (50% oil dispersion, 337 mg) was washed with hexane to remove oil, dried under vacuo and stirred in tetrahydrofuran. The slurry formed was cooled in ice and treated with 2-(n-hexylphenyl)-4-methyl-5-hydroxypyrimidine (2 g) in tetrahydrofuran. The cold mixture was stirred in the cold at 0° C. for 30 minutes and concentrated to a greenish foam. Ethyl alcohol was added and the mixture concentrated. Toluene was added and concentrated to a solid under vacuum. Yield: 2.01 g; m.p. 128°–131° C.

EXAMPLE 20

2-Phenylpentylamino-4,5-dimethyl-5-methoxypyrimidine phosphate 1.09 g of 2-phenylpentylamino-4,6-dimethyl-5-methoxypyrimidine was dissolved in 15 ml isopropylalcohol and cooled to 0° C. Phosphoric acid (85%, 9 g) was added and the mixture stirred at 0° C. for 30 minutes. White solid precipitated and was collected after removal of the isopropylalcohol, washing with pentane and drying in vacuo at 45° C. M.p.: 107°–8° C.

EXAMPLE 21

Similar to the method in Example 20, the following compounds were prepared.

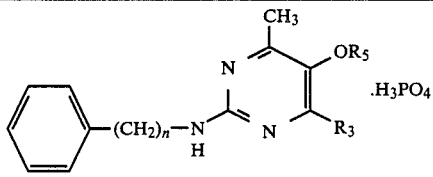

| $R_3$ | $R_5$ | n | Melting Point (°C.) |
|---|---|---|---|
| $CH_3$ | $CH_3$ | 6 | 97–98 |
| $CH_3$ | $CH_3$ | 4 | 96–97 |
| $CH_3$ | $CH_3$ | 3 | 99–100 |
| $CH_3$ | H | 6 | 171–172 |
| $CH_3$ | H | 5 | 167–168 |

We claim:
1. A compound of the formula

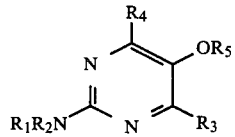

wherein $R_1$ is hydrogen or ($C_1$–$C_{15}$)alkyl; $R_2$ is hydrogen, ($C_1$–$C_{15}$)alkyl, cyclopentyl, cyclohexyl, ($C_3$–$C_{15}$)alkenyl, phenyl, or ($C_7$–$C_{20}$)phenylalkyl which may be substituted in the phenyl by one or two of fluoro, chloro, ($C_1$–$C_3$) alkyl, ($C_1$–$C_3$) alkoxy, or $CF_3$; or $R_1$ and $R_2$ together with the nitrogen atom to which they are attached form a pyrrolidinyl or piperidyl which may be substituted by one ($C_1$–$C_6$)alkyl, phenyl, or ($C_7$–$C_{20}$)phenylalkyl; $R_3$ is ($C_1$–$C_6$)alkyl, phenyl, ($C_7$–$C_{20}$) phenylalkyl which may be substituted in the phenyl by one or two fluoro, chloro, $(C_1-C_3)$alkyl, $(C_1-C_3)$ alkoxy, or $CF_3$, or furyl or thienyl which may be substituted by one $(C_1-C_3)$alkyl; $R_4$ is hydrogen, $(C_1-C_6)$alkyl, phenyl or $(C_7-C_{20})$phenylalkyl which may be substituted in the phenyl by one or two of fluoro. chloro, $(C_1-C_3)$alkyl, $(C_1-C_3)$alkoxy or $CF_3$; and $R_5$ is hydrogen, $(C_1-C_6)$alkyl, phenyl or $(C_7-C_{20})$phenylalkyl which may be substituted in the phenyl by one or two of fluoro, chloro, $(C_1-C_3)$alkyl, $(C_1-C_3)$alkoxy or $CF_3$; with the provision that when $R_5$ is hydrogen and (1) $R_3$ and $R_4$ are each methyl, then $R_1$ and $R_2$ are not each hydrogen, or (2) $R_3$ and $R_4$ are each phenyl, then R1 and $R_2$ are not each methyl, or (3) $R_3$ is $(C_1-C_6)$alkyl, then $R_4$ is not hydrogen;

or an acid or, when $R_5$ is hydrogen, a base addition salt thereof.

2. A compound according to claim 1, where $R_2$ is hydrogen, $(C_1-C_{15})$alkyl, or $(C_7-C_{20})$phenylalkyl which may be substituted in the phenyl by one or two of chloro or $(C_1-C_3)$alkyl; $R_3$ is $(C_1-C_6)$alkyl, phenyl which may be substituted by one or two fluoro, chloro, methyl, ethyl, methoxy, ethoxy, or $CF_3$; and $R_4$ is hydrogen, $(C_1-C_6)$alkyl, phenyl or phenyl substituted by one or two methyl or ethyl.

3. A compound according to claim 1, wherein $R_2$ is $(C_9-C_{12})$phenylalkyl or $(C_8-C_9)$ alkyl.

4. A compound according to claim 1, wherein $R_2$ is $(C_9-C_{12})$p-chlorophenylalkyl.

5. A compound according to claim 1, wherein $R_2$ is $(C_{10}-C_{13})$p-methylphenylalkyl.

6. A compound according to claim 1 wherein $R_1$ and $R_2$ are each $(C_1-C_6)$alkyl. $R_2$ are each $(C_1-C_6)$ alkyl.

7. A compound according to claim 1, wherein $R_3$ and $R_4$ are each methyl.

8. A compound according to claim 1, selected from the group consisting of 2-(p-chlorophenylpropylamino)-4,6-dimethyl-5-hydroxypyrimidine, 2-(p-methylphenylpropylamino)-4,6-dimethyl-5-hydroxypyrimidine, 2-(n-nonylamino)-4,6-dimethyl-5-hydroxypyrimidine, 2-phenylhexylamino-4,6-dimethyl-5-hydroxypyrimidine, and 2-dimethylamino-4-p-fluorophenyl-5-hydroxypyrimidine.

9. A compound according to claim 1 wherein $R_5$ is $(C_1-C_6)$alkyl.

10. A compound according to claim 2 wherein $R_5$ is $(C_1-C_6)$ alkyl.

11. A compound according to claim 1 selected from the group consisting of 2-phenylhexylamino-4-methyl-5-methoxypyrimidine, 2-dimethylamino-4-(3,4-dichlorophenyl)-5-methoxypyrimidine, 2-dimethylamino-4-(3,4-dichlorophenyl)-5-ethoxypyrimidine, 2-(p-chlorophenylpropyl)-4,6-dimethyl-5-methoxypyrimidine, 2-phenylhexylamino-4,6-dimethyl-5-methoxypyrimidine, and 2-phenylpentylamino-4,6-dimethyl-5-methoxypyrimidine.

12. A compound according to claim 1 wherein said acid addition salt is a phosphate addition salt.

13. A composition for the treatment of pulmonary, asthmatic, allergic or inflammatory diseases which comprises a compound of the formula

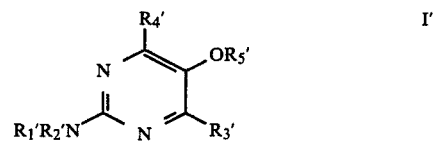

wherein $R_1'$ is hydrogen or $(C_1-C_{15})$alkyl; $R_2'$ is hydrogen, $(C_1-C_{15})$alkyl, cyclopentyl, cyclohexyl, $(C_3-C_{15})$alkenyl, phenyl, or $(C_7-C_{20})$phenylalkyl which may be substituted in the phenyl by one or two of fluoro, chloro, $(C_1-C_3)$ alkyl, $(C_1-C_3)$ alkoxy, or $CF_3$; or $R_1'$ and $R_2'$ together with the nitrogen atom to which they are attached form a pyrrolidinyl or piperidyl which may be substituted by one $(C_1-C_6)$alkyl, phenyl, or $(C_7-C_{20})$phenylalkyl; $R_3'$ is $(C_1-C_6)$alkyl, phenyl, $(C_7-C_{20})$phenylalkyl which may be substituted in the phenyl group by one or two fluoro, chloro, $(C_1-C_3)$alkyl, $(C_1-C_3)$alkoxy, or $CF_3$, or furyl or thienyl which may be substituted by one $(C_1-C_3)$alkyl; $R_4'$ is hydrogen, $(C_1-C_6)$alkyl, phenyl or $(C_7-C_{20})$phenylalkyl which may be substituted in the phenyl group by one or two fluoro, chloro, $(C_1-C_3)$alkyl, $(C_1-C_3)$alkoxy or $CF_3$; and $R_5'$ is hydrogen, $(C_1-C_6)$alkyl, or $(C_7-C_{20})$phenylalkyl which may be substituted in the phenyl group by one to three of fluoro, chloro, $(C_1-C_3)$alkyl, $(C_1-C_3)$alkoxy or $CF_3$; with the proviso that when $R_4'$ and $R_5'$ are each hydrogen then $R_3'$ is not $(C_1-C_6)$alkyl;

or a pharmaceutically acceptable acid salt thereof or, when $R_5'$ is hydrogen, a pharmaceutically acceptable base addition salt thereof, in an amount effective for the treatment of said diseases, in admixture with a pharmaceutically acceptable carrier.

14. A composition according to claim 13, wherein $R_2'$ is hydrogen, $(C_1-C_{15})$alkyl, phenyl, or $(C_7-C_{20})$ phenylalkyl which may be substituted in the phenyl by one or two chloro or $(C_1-C_3)$alkyl; $R_3'$ is $(C_1-C_6)$alkyl, phenyl which may be substituted by one or two fluoro, chloro, methyl, ethyl, methoxy, ethoxy, or $CF_3$; and $R_4'$ is hydrogen, $(C_1-C_6)$alkyl, phenyl or phenyl substituted by one or two methyl or ethyl.

15. A composition according to claim 13, wherein $R_3'$ and $R_4'$ are each methyl.

16. A composition according to claim 13, wherein said compound is selected from the group consisting of 2-(p-chlorophenylpropylamino)-4,6-dimethyl-5-hydroxypyrimidine, 2-(p-methylphenylpropylamino)-4,6-dimethyl5-hydroxypyrimidine, 2-(n-nonylamino)-4,6-dimethyl-5-hydroxypyrimidine, 2-phenylhexyl-4,6-dimethyl-5-hydroxy-pyrimidine, and 2-dimethylamino-4-p-fluoro-phenyl-5-hydroxypyrimidine.

17. A method for the treatment of pulmonary, asthmatic, allergic or inflammatory diseases which comprises administering to a host in need of such treatment a compound of the formula I', as defined in claim 13 or a pharmaceutically acceptable acid addition salt thereof or, when $R_5'$ is hydrogen, a pharmaceutically acceptable base addition salt thereof.

* * * * *